US006960179B2

(12) United States Patent
Gura

(10) Patent No.: US 6,960,179 B2
(45) Date of Patent: Nov. 1, 2005

(54) WEARABLE CONTINUOUS RENAL REPLACEMENT THERAPY DEVICE

(75) Inventor: Victor Gura, Beverly Hills, CA (US)

(73) Assignee: National Quality Care, INC, Beverly Hills, CA (US)

( * ) Notice: Subject to any disclaimer, the term of this patent is extended or adjusted under 35 U.S.C. 154(b) by 261 days.

(21) Appl. No.: 10/085,349

(22) Filed: Nov. 16, 2001

(65) Prior Publication Data

US 2003/0097086 A1 May 22, 2003

(51) Int. Cl.$^7$ .................... A61M 37/00; C02F 1/44
(52) U.S. Cl. ............... 604/6.09; 604/5.04; 210/645; 210/646; 210/321.8; 210/321.89
(58) Field of Search ................... 604/5.04, 6.05, 604/6.06, 6.09, 6.11, 6.14, 6.15, 6.16, 65–67; 210/645, 646, 739, 321.75–81, 321.84–9, 322, 500.1, 500.21

(56) References Cited

U.S. PATENT DOCUMENTS

| | | | |
|---|---|---|---|
| 3,388,803 A | 6/1968 | Scott | |
| 3,746,175 A | 7/1973 | Markley | |
| 3,884,808 A | 5/1975 | Scott | 210/109 |
| 3,994,799 A | 11/1976 | Yao et al. | |
| 4,094,775 A | 6/1978 | Mueller | |
| 4,212,738 A | 7/1980 | Henne | 210/94 |
| 4,247,393 A | 1/1981 | Wallace | 210/638 |
| 4,267,040 A | 5/1981 | Schäl | 210/104 |
| 4,269,708 A | 5/1981 | Bonomini et al. | 210/90 |
| 4,443,333 A | 4/1984 | Mahurkar | 210/87 |
| 4,765,907 A | 8/1988 | Scott | 210/648 |
| 4,897,189 A * | 1/1990 | Greenwood et al. | 210/195.2 |
| 4,997,570 A | 3/1991 | Polaschegg | 210/646 |
| 5,284,470 A | 2/1994 | Beltz | 604/4 |
| 5,902,336 A | 5/1999 | Mishkin | 623/11 |
| 5,944,684 A | 8/1999 | Roberts et al. | 604/5 |
| 5,984,891 A | 11/1999 | Keilman et al. | |
| 6,117,100 A | 9/2000 | Powers et al. | 604/4 |
| 6,117,122 A * | 9/2000 | Din et al. | 604/408 |
| 6,196,992 B1 | 3/2001 | Keilman et al. | |
| 6,332,985 B1 | 12/2001 | Sherman et al. | 210/638 |
| 6,406,631 B1 * | 6/2002 | Collins et al. | 210/646 |
| 6,796,955 B2 | 9/2004 | O'Mahony et al. | |

OTHER PUBLICATIONS

PCT Notification of Transmittal of the International Search Report dated Nov. 3, 2003.
Manns, Markus, et al., "The acu–men: A new device for continous renal replacement therapy in acute renal failure," Kidney International, vol. 54:pp. 268–274 (1998).
Martin Roberts, "Wearable Artificial Kidneys for Continous Dialysis," ASAIO Journal, 1993, p. 19–23.
A. Murisasco, et al; "Continuous Arterio–venous Hemofiltration in a Wearable Device to Treat End–stage Renal Disease," Trans Am Soc Artif Intern Organs, vol. XXXII, 1986, pp. 567.
A. Murisasco, et al, "A Continuous Hemofiltration System Using Sorbents for Hemofiltrate Regeneration," Clinical Nephrology, vol. 26, Supp. No. 1—1986, pps. S53–S57.
Arnold J. Lande' , et al, "In Search of a 24 Hours Per Day Artificial Kidney," Journal of Dialysis, 1(8), 1977, pps. 805–823.

* cited by examiner

Primary Examiner—Angela D. Sykes
Assistant Examiner—Leslie R. Deak
(74) Attorney, Agent, or Firm—Jenkens & Gilchrist

(57) ABSTRACT

A continuous renal replacement therapy device adapted to be worn on a portion of the body of a patient, including: a plurality of contoured dialyzers, which are connected in series and utilize dialysate to remove impurities from the blood of the patient; and a plurality of contoured sorbent device, which are connected in series and are for regenerating the spent dialysate.

33 Claims, 5 Drawing Sheets

WEARABLE CONTINUOUS RENAL REPLACEMENT THERAPY DEVICE

FIELD OF THE INVENTION

The present invention is directed to dialysis systems, and more particularly to a dialysis system that may be continuously worn by a patient.

BACKGROUND OF THE INVENTION

Hemodialysis is a process by which microscopic toxins are removed from the blood using a filtering membrane such as a dialyzer. Typically, hemodialysis is administered in intermittent three to four hours sessions, which take place two or three times per week. However, there exists a growing body of research that prefers continuous renal replacement therapy (CRRT) over intermittent dialysis since far more toxins can be removed from the blood using CRRT seven days a week, twenty-four hours a day. Some advantages of CRRT include a decreased rate of morbidity and expected mortality, a decrease in the amount of medications required and a decrease in fluid intake and dietary restrictions.

CRRT utilizes machines that provide around the clock dialysis, hemofiltration or a combination of both. However, CRRT machines are cumbersome, heavy and must be hooked to electrical outlets and several feet of tubing. In addition, these machines require a continuous supply of gallons of fresh dialysate fluid. Further, a CRRT patient must remain connected to the CRRT machine for many hours, limiting his or her ability to perform normal every day activities.

An addition problem with CRRT, is that daily reconnection to the CRRT machine requires accessing blood flow by puncturing a large blood vessel forming an arteriovenous shunt. These shunts only last for limited periods of time and are subject to infection, clotting and other complications that result in numerous hospitalizations and repeated surgical interventions.

Unsuccessful attempts have been made to create a wearable dialysis device employing the idea of CRRT. Because of the bulky nature of typical dialyzers and associated sorbent devices, the concept of a wearable CRRT device has yet to become a reality for most dialysis patients. In view of the above disadvantages, there continues to be a substantial need for a portable, wearable CRRT device, which can which can be used continually, 24 hours a day, seven days a week.

SUMMARY OF THE INVENTION

One aspect of the present invention involves a CRRT device adapted to be worn on a portion of the body of a patient, including a plurality of dialyzers connected in series that utilize dialysate to remove impurities from the blood of the patient and at least one sorbent device for regenerating the spent dialysate.

Another aspect of the present invention involves a CRRT device adapted to be worn on a portion of the body of a patient, including a plurality of dialyzers, which comprise a plurality of cylindrical hollow fibers; wherein the patient's blood is circulated within the hollow fibers in a first direction and wherein the dialysate is circulated around the exterior walls of the hollow fibers in a second, opposite direction; wherein the exterior walls of the hollow fibers are semiporous so that impurities can be moved from the blood and into the dialysate.

An additional aspect of the present invention involves a CRRT device adapted to be worn on a portion of the body of a patient, including a plurality of dialyzers, which comprise a plurality of parallel sheets of semiporous material, wherein the patient's blood is circulated on one side of the parallel sheets in a first direction and wherein the dialysate is circulated on the other side of the parallel sheets in a second, opposite direction.

A further aspect of the present invention involves a CRRT device adapted to be worn on a portion of the body of a patient, including a plurality of dialyzers; wherein the number of dialyzers in the plurality of dialyzers may be varied to reflect different dialysis prescriptions; wherein each of the plurality of dialyzers has a flexible casing adapted to conform to the body contour of the patient.

Yet another aspect of the present invention involves a CRRT device adapted to be worn on a portion of the body of a patient, including a plurality of dialyzers having a blood inlet tube with a side port for the infusion of additives; wherein the additives are pumped into the blood from a plurality of additive reservoirs and the rate of infusion of each additive is controlled electronically.

Another aspect of the present invention involves a CRRT device adapted to be worn on a portion of the body of a patient, including at least one dialyzer that utilizes dialysate to remove impurities from the blood of the patient and a plurality of sorbent devices connected in series for regenerating the dialysate.

A further aspect of the present invention involves a CRRT device adapted to be worn on a portion of the body of a patient, including a plurality of sorbent devices; wherein each of the sorbent devices has a flexible casing adapted to conform to the body contour of the patient.

An additional aspect of the present invention involves a CRRT device adapted to be worn on a portion of the body of a patient, including a series of sorbent devices; wherein the series of sorbent devices is a series of replaceable cartridges, which may include activated charcoal, urease, zirconium phosphate, hydrous zirconium oxide and/or activated carbon.

A further aspect of the present invention involves a CRRT device adapted to be worn on a portion of the body of a patient, include a plurality of dialyzers connected in parallel.

Yet another aspect of the present invention involves a CRRT device adapted to be worn on a portion of the body of a patient, include a plurality of sorbent devices connected in parallel.

Further applicability of the present invention will become apparent from a review of the detailed description and accompanying drawings. It should be understood that the description and examples, while indicating preferred embodiments of the present invention, are not intended to limit the scope of the invention, and various changes and modifications within the spirit and scope of the invention will become apparent to those skilled in the art.

BRIEF DESCRIPTION OF THE DRAWINGS

The present invention will become more fully understood from the detailed description given below, together with the accompanying drawings, which are given by way of illustration only, and are not to be construed as limiting the scope of the present invention. In the drawings.

DETAILED DESCRIPTION OF THE PREFERRED EMBODIMENTS

Figure 1:
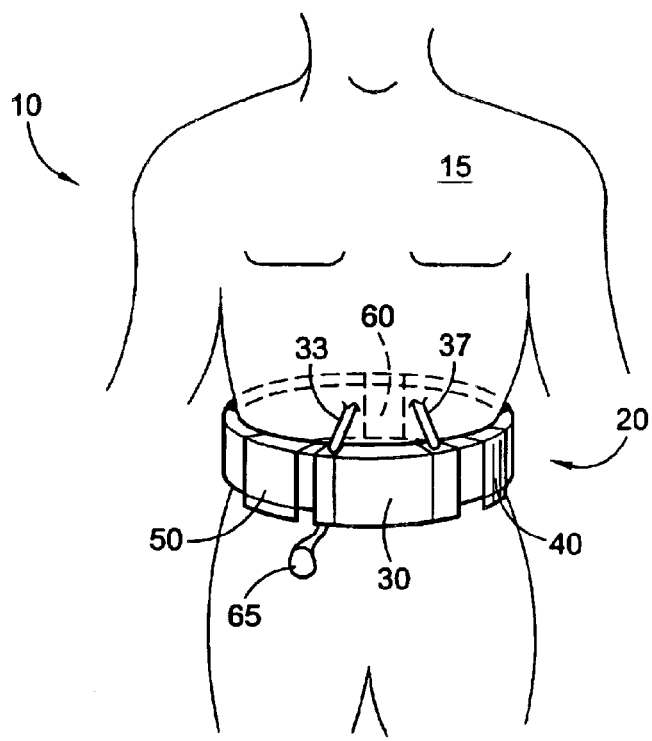
FIG. 1 is a perspective view of the wearable CRRT device worn around the waist of a dialysis patient according to the present invention.

Before starting a description of the Figures, instructions for interpreting the words and phrases of this patent document will be provided. More particularly, many jurisdictions allow a patentee to act as its own lexicographer, and thereby allow the patentee to provide instructions in a patent document as to how the words, terms and phrases of the document are to be interpreted as a legal matter. For example, in the United States, the prerogative of the patentee to act as its own lexicographer has been solidly established based on statutory and case law. Accordingly, the following section provides rules for interpreting the words, terms and phrases of this particular patent document.

Interpretive Rules

Rule 1: There is a "Specially Defined Terms" section set forth below. Only words, terms or phrases that are explicitly defined in the Specially Defined Terms are to be considered to have a special definition, and, of course, the explicit definition provided herein is to serve as the definition for these terms. Accordingly, sources such as the patent specification and extrinsic evidence shall not be used to help define these terms—the explicitly provided definitions shall control.

Rule 2: If a word, term or phrase is not specially defined, then its definition shall be determined in the first instance by resort to dictionaries and technical lexicons that either exist as of the time this patent document is filed. (See definition of "dictionaries and technical lexicons" below in the Specially defined Terms section.) It is acknowledged that dictionaries and technical lexicons often provide alternative definitions. Also, definitions provided in different dictionaries and different lexicons often differ and are not always entirely consistent. In that case, it must be decided which definition is in best accordance with this document. Rules 3 and 4, set forth below, provide some guidelines for choosing between alternative definitions for a word, term or phrase.

Rule 3: The role of the specification (other than the Specially Defined Terms section) as an interpretive or definitional aid shall be limited to helping choose between alternative definitions that meet the requirements of Rule 2 (above).

Rule 4: The role of extrinsic evidence (e.g., expert witnesses) as an interpretive or definitional aid shall be limited to helping choose between alternative definitions that meet the requirements of Rule 2 (above).

Specially Defined Terms the present invention: means at least some embodiments of the present invention; references to various feature(s) of the "present invention" throughout this document do not mean that all claimed embodiments or methods include the referenced feature(s).

dictionaries and/or technical lexicons: any document whose primary purpose is the definition of words, terms and/or phrases; on the other hand, documents that merely discuss, explain or provide examples of devices or methods, without purporting to provide definitions of specific words, phrases or terms, are not to be considered as dictionaries and/or technical lexicons.

hemodialysis: a process by which microscopic toxins are moved from one side of a filtering membrane (such as a dialyzer, e.g.) to another, wherein waste products and excess chemicals (including, but not limited to electrolytes) in the blood pass through the membrane into a solution (such as dialysate, e.g.) that does not contain those toxins.

dialysate: a fluid used for dialysis that may consist of a mixture of water, glucose, and certain elements (including, but not limited to electrolytes). During dialysis, waste products and excess chemicals in the blood pass through a filtering membrane (such as a dialyzer, e.g.) into the dialysate fluid.

dialyzer: a filtering membrane used to filer waste products and excess chemicals (including, but not limited to electrolytes) during dialysis. Typically, a dialyzer is an artificial kidney that contains many hollow membrane fibers surrounded by dialysate. While blood flows inside of the hollow membranes, toxins from the blood move through the membrane wall and into the dialysate. The purified blood remains inside the hollow membranes and is returned to the body.

To the extent that the definitions provided above are consistent with ordinary, plain and accustomed meanings (as generally evidenced, inter alia, by dictionaries and/or technical lexicons), the above definitions shall be considered supplemental in nature. To the extent that the definitions provided above are inconsistent with ordinary, plain and accustomed meanings (as generally evidenced, inter alia, by dictionaries and/or technical lexicons), the above definitions shall control. If the definitions provided above are broader than the ordinary, plain and accustomed meanings in some aspect, then the above definitions will control at least in relation to their broader aspects.

To the extent that a patentee may act as its own lexicographer under applicable law, it is hereby further directed that all words appearing in the claims section, except for the above-defined words, shall take on their ordinary, plain and accustomed meanings (as generally evidenced, inter alia, by dictionaries and/or technical lexicons), and shall not be considered to be specially defined in this specification. Notwithstanding this limitation on the inference of "special definitions," the specification may be used to evidence the appropriate ordinary, plain and accustomed meanings (as generally evidenced, inter alia, by dictionaries and/or technical lexicons), in the situation where a word or term used in the claims has more than one alternative ordinary, plain and accustomed meaning and the specification is helpful in choosing between the alternatives.

Figure 2:
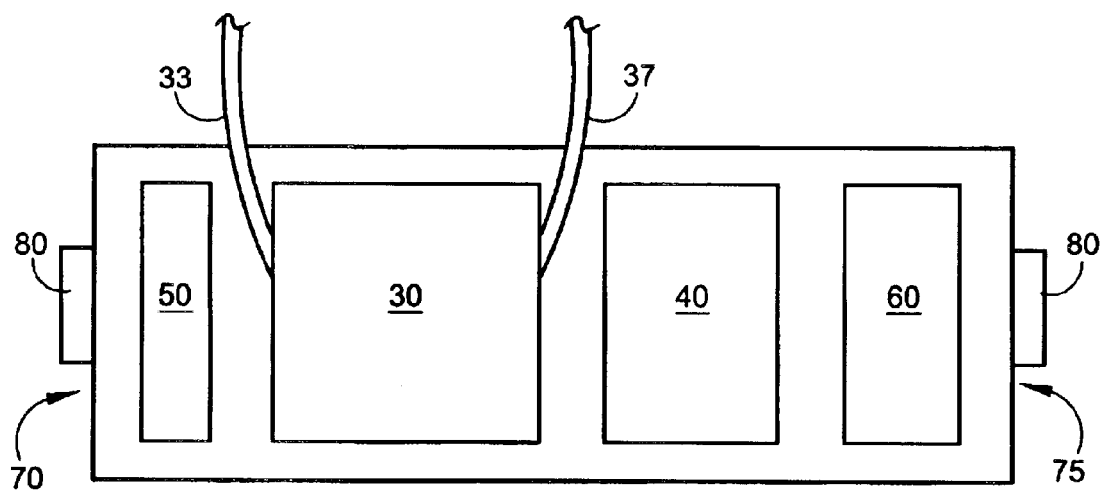
FIG. 2 is a front view of the wearable CRRT device of FIG. 1 after being detached from the dialysis patient.

Referring to FIGS. 1 and 2, a continuous renal replacement therapy (CRRT) device 10 is adapted to be worn about a portion of the body of a dialysis patient 15. The CRRT device 10 includes a belt 20 that is divided into a number of sections comprising: a dialyzer section 30 including a blood inlet tube 33 leading from a blood vessel and a blood outlet tube leading to a blood vessel; a sorbent section 40; an additive pump section 50; and an electronic control section 60, which includes a microprocessor and batteries to power device 10.

As best seen in FIG. 2, the belt 20 includes a pair of end portions 70, 75, which are secured together by a conventional belt fastener 80 such as a buckle, snaps, buttons or hook and loop fasteners. Although the CRRT device 10 depicted in FIG. 1 is worn about the waist of the patient 15, it should be understood to those of ordinary skill in the art that the device 10 may, alternatively, be worn about other portions of the patient's body, such as over a shoulder of the patient, for example.

Figure 3:
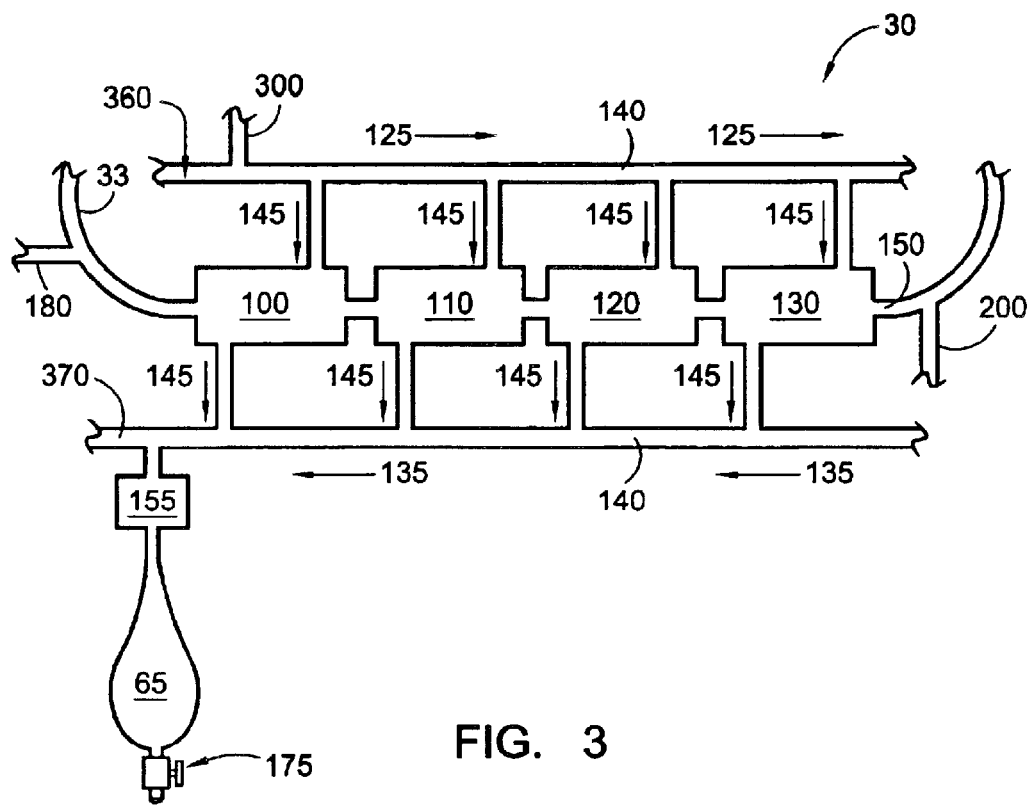
FIG. 3 is a perspective view of the dialyzer section of the wearable CRRT device according to the present invention.

Referring to FIG. 3, the dialyzer section 30 of the belt 20 includes a plurality of miniaturized dialyzers 100, 110, 120, 130 that utilize dialysate fluid 140 to remove impurities from the blood 150 of the patient 15. The number of dialyzers 100, 110, 120, 130 in the plurality of dialyzers 100, 110, 120, 130 may be varied to reflect different dialysis prescriptions. As best seen in FIG. 3, the plurality of dialyzers 100, 110, 120, 130 are connected in series, whereby a conventional pump forces the patient's blood 150 through a blood inlet tube 33, through the dialyzers 100, 110, 120, 130 and into blood outlet tube 37. It should be understood to those of ordinary skill in the art that the dialyzers 100, 110, 120, 130 could also be connected in parallel without departing from the scope of the invention.

During dialysis, the dialysate is pumped in the opposite direction of the blood flow using a conventional pump (not shown) as indicated by arrows 125, 135, 145. Spent dialysate 140 flows toward sorbent section 40 through spent dialysate tube 370. Excess fluid is removed from the spent dialysate 140 through a volumetric chamber 155 and into a waste receiver 65, which is to be periodically emptied by the patient via tap 175. A microprocessor in the electronic section 60 determines the rate and amount of fluid removal through volumetric chamber 155.

Figure 4:
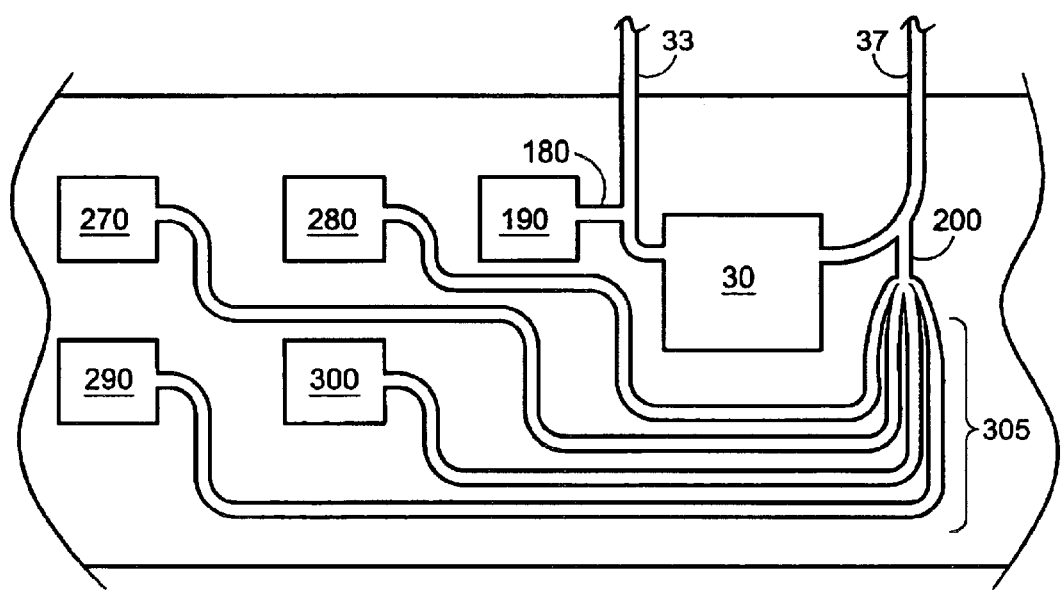
FIG. 4 is a perspective view of the additive pump and dialyzer sections of the wearable CRRT device according to the present invention.

With further reference to FIG. 3, the blood inlet tube 33 includes a side port 180 through which anticoagulant is pumped into the blood by anticoagulant pump 190. Typical anticoagulants are infused into the blood 150 include, but are not limited to, heparin, prostacyclin, low molecular weight heparin, hirudin and sodium citrate. As best seen in FIG. 4, the blood outlet tube 37 includes a side port 200 for the infusion of additives, which are forced into the blood 150 from a plurality of additive pumps 270, 280, 290, 300. Piston, suction or roller pumps can be employed for this purpose. Each additive pump 270, 280, 290, 300 forces a controlled amount of respective additive into the blood 150, wherein the rate of infusion of each additive is controlled electronically by the microprocessor in the electronic control section 60. In a known manner, a physician can use the electronic control section 60 to set the rate of infusion for each additive to correspond to a predetermined dose for each additive. Since the additives cannot be mixed together prior to infusion in the blood 150, they have separate circuits 305. Typical additives include, but are not limited to, sodium citrate, calcium, potassium and sodium bicarbonate.

Figure 5:
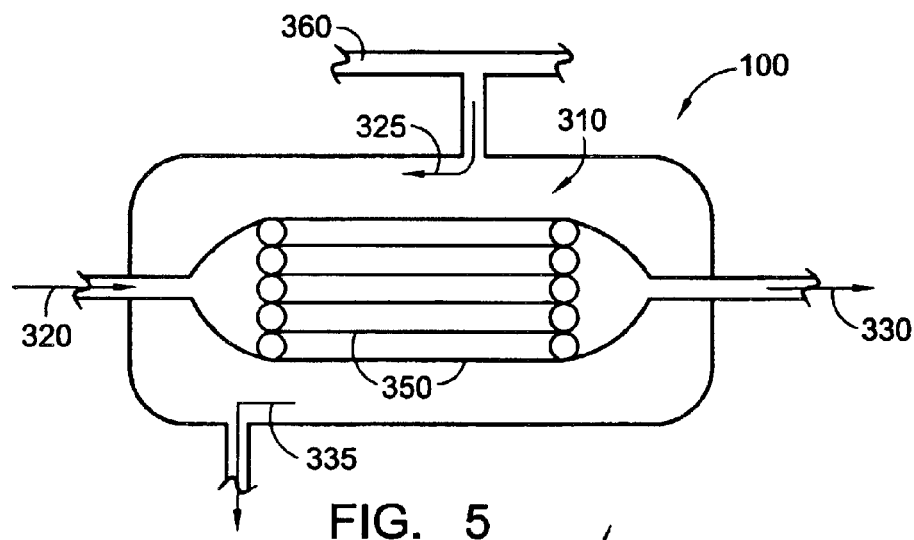
FIG. 5 is a cross-sectional view of a first embodiment of a dialyzer of the wearable CRRT device according to the present invention.
Figure 6:
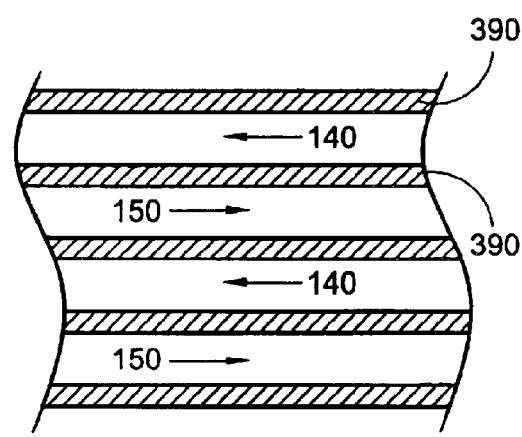
FIG. 6 is a cross-sectional view of a second embodiment of a dialyzer of the wearable CRRT device according to the present invention.

Referring to FIG. 5, in a first dialyzer embodiment, each dialyzer 100, 110, 120, 130 is a conventional dialyzer comprising a plurality of cylindrical hollow fibers 310 through which the blood 150 is circulated. As indicated by arrows 320, 330, the dialysate fluid 140 is circulated around exterior walls 350 of the hollow fibers 310 in a direction across the blood flow inside the hollow fibers 310 as indicated by arrows 325, 335. The exterior walls 350 of the hollow fibers 310 are semiporous so that impurities can be moved from the blood 150 and into the dialysate 140. Fresh dialysate 140 flows from the sorbent section 40 through a dialysate inlet tube 360 and into the series of dialyzers 100, 110, 120, 130. The spent dialysate 140 then flows out of the series of dialyzers 100, 110, 120, 130, through a spent dialysate outlet tube 370 and into the sorbent section 40. The dialysate inlet tube 360 includes a side port 380 (shown in FIG. 3) for the infusion of additives, which can be forced into the blood 150 via the aforementioned additive pumps 270, 280, 290, 300, whereby the rate of infusion is controlled electronically by the microprocessor in the electronic control section 60. Referring to FIG. 6, in second dialyzer embodiment, each dialyzer 100, 110, 120, 130 comprises a plurality of parallel sheets 390 of semiporous material, wherein the dialysate fluid 140 is circulated on one side of the parallel sheets 390 and the blood 150 circulates in the direction on the other side of the parallel sheets 390. The dialyzers of each embodiment are conventional and well known in the art.

Figures 7, 11:
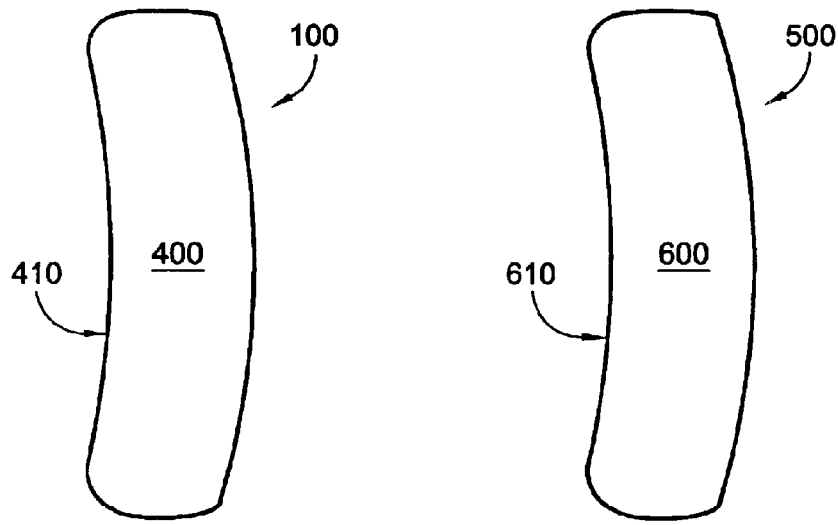
FIG. 7 is a top view of a casing of a dialyzer of the wearable CRRT device according to the present invention.
FIG. 11 is a top view of a casing of a sorbent device of the wearable CRRT device according to the present invention.

Referring to FIG. 7, each dialyzer 100, 110, 120, 130 is a miniature dialyzer having a flexible casing 400 adapted to conform to the body contour of the patient. In addition, the body-side wall 410 of each casing 400 is concave to further correspond to bodily curves of the user. The casing 400 can be made of any suitable material having adequate flexibility for conformance to the portion of the body to which it is applied. Suitable materials include, but are not limited to polyurethane and poly vinyl chloride.

Figure 8:
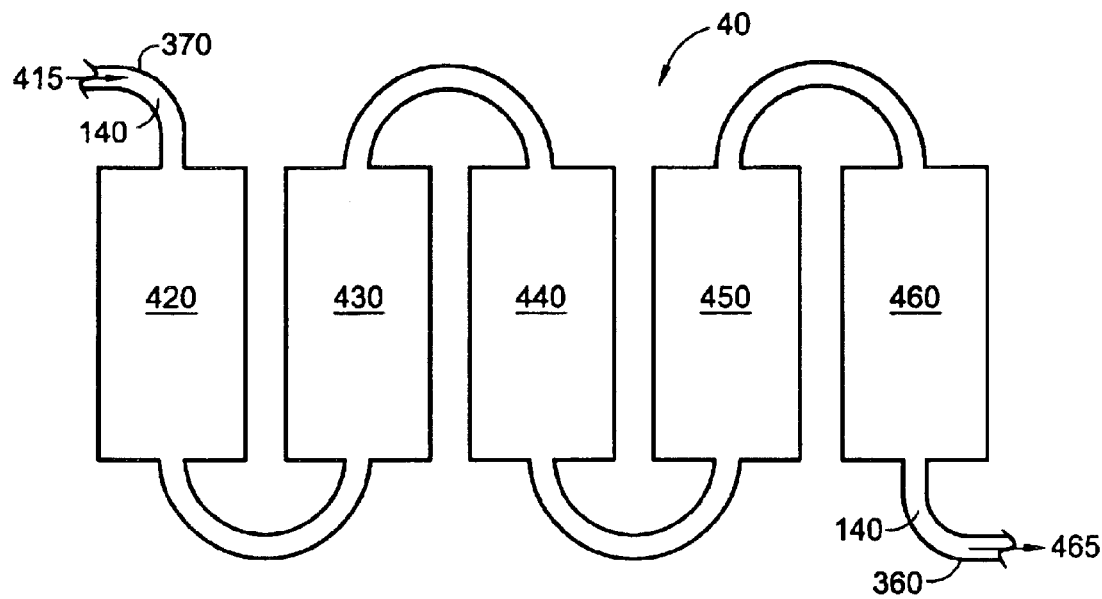
FIG. 8 is a perspective view of a first embodiment of the sorbent section of the wearable CRRT device according to the present invention.
Figure 9:
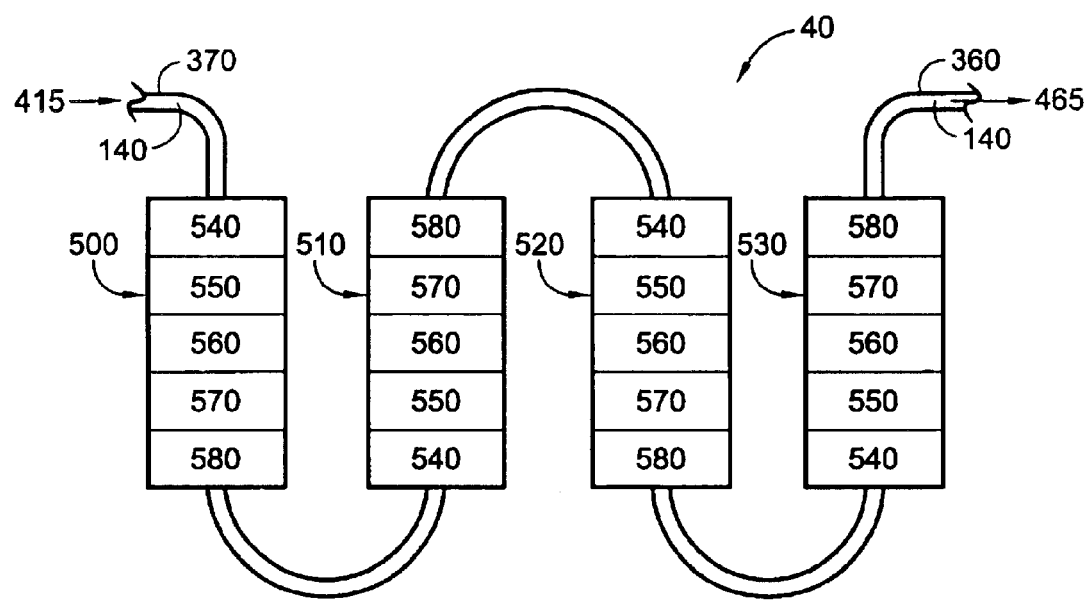
FIG. 9 is a perspective view of a second embodiment of the sorbent section of the wearable CRRT device according to the present invention.
Figure 10:
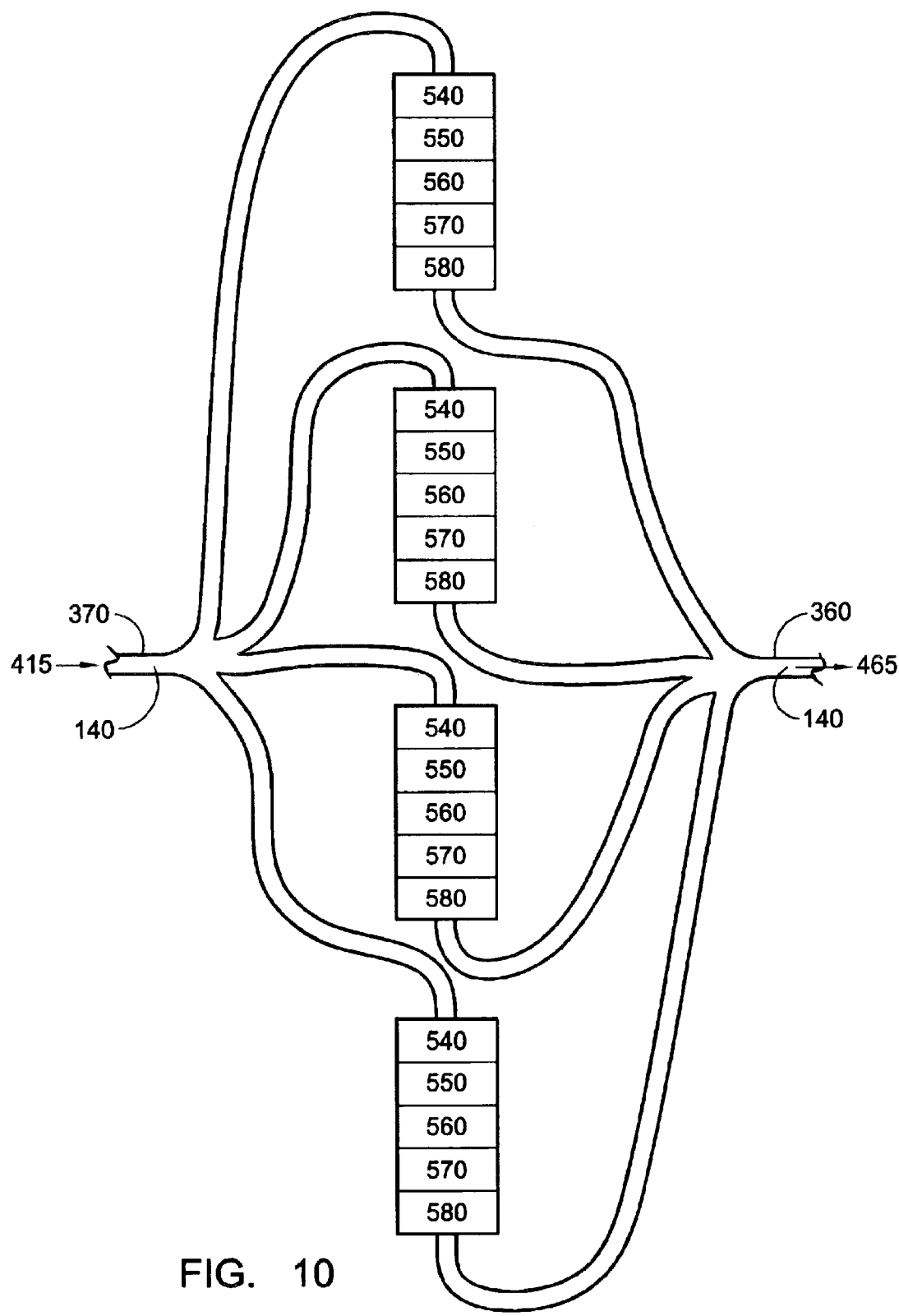
FIG. 10 is a perspective view of a variation of the second embodiment of the sorbent section of the wearable CRRT device according to the present invention.

Referring to FIGS. 8–10, in the sorbent section 40, as indicated by arrow 415, spent dialysate 140 flows from the dialyzer section 30 through spent dialysate tube 370 and into a plurality of sorbent devices 420, 430, 440, 450, 460. As indicated by arrow 465, the regenerated dialysate 140 then flows through tube 360 and back into the dialyzer section 30. Preferably, the sorbent devices 420, 430, 440, 450, 460 comprise a series of sorbent cartridges 420, 430, 440, 450, 460 for regenerating the spent dialysate 140. By regenerating the dialysate with sorbent cartridges 420, 430, 440, 450, 460, the CRRT device 10 of the present invention requires only a small fraction of the amount of dialysate of a single-pass hemodialysis device. Importantly, each sorbent cartridge 420, 430, 440, 450, 460 is a miniaturized sorbent cartridge 420, 430, 440, 450, 460 containing a distinct sorbent.

Referring to FIG. 8, in a first embodiment of the sorbent section 40, there are five sorbent cartridges 420, 430, 440, 450, 460 including an activated charcoal cartridge 420, a urease cartridge 430, a zirconium phosphate cartridge 440, a hydrous zirconium oxide cartridge 450 and an activated carbon cartridge 460. Those of ordinary skill in the art will recognize that these sorbents are similar to the sorbents employed by the commercially available Recirculating Dialysis (REDY) System. However, in the REDY System, the sorbents are layers of a single cartridge. By contrast, the sorbents of the present invention are each part of a distinct sorbent cartridge 420, 430, 440, 450, 460 such that each cartridge 420, 430, 440, 450, 460 may, conveniently, be replaced and disposed of independently of the other cartridges 420, 430, 440, 450, 460. As one of ordinary skill in the art would understand, activated charcoal, urease, zirconium phosphate, hydrous zirconium oxide and activated carbon are not the only chemicals that could be used as sorbents in the present CRRT device 10. In fact, any number of additional or alternative sorbents could be employed without departing from the scope of the present invention.

Referring to FIGS. 9 and 10, in a second embodiment of the sorbent section 40, there are a plurality of sorbent cartridges 500, 510, 520, 530, wherein each cartridge 500, 510, 520, 530 includes a plurality of sorbent layers 540, 550, 560, 570, 580: an activated charcoal layer 540, a urease layer 550, a zirconium phosphate layer 560, a hydrous zirconium oxide layer 570 and an activated carbon layer 580. The cartridges 500, 510, 520, 530 may be in series as depicted in FIG. 9 or may be in parallel as depicted in FIG. 10. In this embodiment, the number of sorbent devices may be varied to correspond with different dialysis prescriptions.

Referring to FIG. 11, each cartridge 500, 510, 520, 530 is a miniature cartridge having a flexible casing 600 adapted to conform to the body contour of the patient. In addition, the body-side wall 610 of each casing 600 is concave to further correspond to bodily curves. The casing 600 can be made of any suitable material having adequate flexibility for conformance to the portion of the body to which it is applied. Suitable materials include, but are not limited to polyurethane and poly vinyl chloride.

Many variations on the above-described invention are possible. Such variations are not to be regarded as a departure from the spirit and scope of the invention, but rather as subject matter intended to be encompassed within the scope of the following claims, to the fullest extent allowed by applicable law.

What is claimed is:

1. A continuous renal replacement therapy device, comprising:
   at least one dialyzer that utilizes a dialysate to remove impurities from the blood of a patient;
   a microprocessor configured to control a rate of ultrafiltration at the same time said at least one dialyzer is removing impurities from the blood, wherein the device is configured to allow concurrent ultrafiltration and dialysis; and
   at least one dialysate sorbent device for regenerating the dialysate, the entire continuous renal replacement device for being worn on the patient.

2. The continuous renal replacement therapy device of claim 1, wherein the at least one dialyzer is connected in series with at least one additional dialyzer.

3. The continuous renal replacement therapy device of claim 1, wherein at least one of the dialyzers comprises a plurality of cylindrical hollow fibers, wherein the patient's blood is circulated within the hollow fibers in a first direction and wherein the dialysate is circulated around at least a portion of the exterior walls of the hollow fibers in a second direction.

4. The continuous renal replacement therapy device of claim 3, wherein the exterior walls of the hollow fibers are semiporous so that impurities can be moved from the blood and into the dialysate.

5. The continuous renal replacement therapy device of claim 1, wherein each of the at least one dialyzers have a flexible casing adapted to conform to the body contour of the patient.

6. The continuous renal replacement therapy device of claim 1, wherein the number of dialyzers in the at least one dialyzer may be varied to reflect different dialysis prescriptions.

7. The continuous renal replacement therapy device of claim 1, further including a blood inlet tube leading into a first dialyzer of the at least one dialyzer and a blood outlet tube leading out of a last dialyzer of said at least one dialyzer such that the at least one dialyzers are connected in series.

8. The continuous renal replacement therapy device of claim 7, wherein the blood inlet tube includes a side port for the infusion of anticoagulants into the blood.

9. The continuous renal replacement therapy device of claim 8, wherein the anticoagulant is chosen from the group consisting of: heparin, prostacyclin, low molecular weight heparin, hirudin and sodium citrate.

10. The continuous renal replacement therapy device of claim 7, wherein the blood outlet tube includes a side port adapted for an infusion of at least one additive.

11. The continuous renal replacement therapy device of claim 10, wherein the at least one additive can be pumped into the blood by a plurality of additive pumps.

12. The continuous renal replacement therapy device of claim 11, wherein the rate of infusion of said at least one additive is controlled electronically.

13. The continuous renal replacement therapy device of claim 10, wherein said at least one additive is chosen from the group consisting of: sodium citrate, calcium, potassium and sodium bicarbonate.

14. The continuous renal replacement therapy device of claim 1, wherein the at least one sorbent device comprises a plurality of sorbent devices connected in series.

15. The continuous renal replacement therapy device of claim 1, wherein the at least one sorbent device comprises a plurality of sorbent devices connected in parallel.

16. The continuous renal replacement therapy device of claim 1, wherein the at least one dialyzer is connected in parallel with at least one additional dialyzer.

17. The continuous renal replacement therapy device of claim 1, wherein at least one of said at least one dialyzer comprises a plurality of parallel sheets of semiporous material, wherein the patient's blood is circulated on one side of the parallel sheets in a first direction and wherein the dialysate is circulated on the other side of the parallel sheets in a second direction.

18. A continuous renal replacement therapy device, comprising:
    at least one dialyzer that utilizes a dialysate to remove impurities from the blood of a patient;
    a microprocessor programmed to control a rate that excess fluid is removed from dialysate while said at least one dialyzer is removing impurities from the blood, wherein the device is programmed to allow concurrent ultrafiltration and dialysis; and
    a plurality of dialysate sorbent devices for regenerating the dialysate wherein a first sorbent device contains a first sorbent and a second sorbent device that contains a second sorbent; said first sorbent and said second sorbent being different compounds, said entire continuous renal replacement device to be worn on the patient.

19. The continuous renal replacement therapy device of claim 18, wherein the plurality of sorbent devices are connected at least in series.

20. The continuous renal replacement therapy device of claim 18, wherein each of the sorbent devices has a flexible casing adapted to conform to the body contour of the patient.

21. The continuous renal replacement therapy device of claim 18, wherein the number of sorbent devices may be varied to reflect different dialysis prescriptions.

22. The continuous renal replacement therapy device of claim 18, further including a regenerated dialysate inlet tube leading into the at least one dialyzer and a spent dialysate outlet tube leading out of the at least one dialyzer.

23. The continuous renal replacement therapy device of claim 22, wherein the regenerated dialysate inlet tube includes a side port for an infusion of at least one additive.

24. The continuous renal replacement therapy device of claim 23, wherein the at least one additive is pumped into the dialysate from a plurality of additive reservoirs.

25. The continuous renal replacement therapy device of claim 24, wherein the rate of infusion of each one of the at least one additive is controlled electronically.

26. The continuous renal replacement therapy device of claim 23, wherein the at least one additive is chosen from the group consisting of: sodium citrate, calcium, potassium and sodium bicarbonate.

27. The continuous renal replacement therapy device of claim 22, wherein the spent dialysate tube leads into the plurality of sorbent devices and the regenerated dialysate tube leads out of the plurality of sorbent devices.

28. The continuous renal replacement therapy device of claim 19, wherein the series of sorbent devices comprises a series of replaceable cartridges.

29. The continuous renal replacement therapy device of claim 28, wherein the replaceable cartridges include at least one of: activated charcoal, urease, zirconium phosphate, hydrous zirconium oxide and activated carbon.

30. The continuous renal replacement therapy device of claim 18, wherein the at least one sorbent device comprises a plurality of sorbent devices connected in parallel.

31. The continuous renal replacement therapy device of claim 18, wherein the at least one dialyzer comprises a plurality of dialyzers connected in parallel.

32. The continuous renal replacement therapy device of claim 18, wherein the at least one dialyzer comprises a plurality of dialyzers connected in series.

33. The continuous renal replacement therapy device of claim 32, wherein at least one of the at least one dialyzer comprises a plurality of parallel sheets of semiporous material, wherein the patient's blood is circulated on one side of the parallel sheets in a first direction and wherein the dialysate is circulated on the other side of the parallel sheets in a second direction.

* * * * *